United States Patent [19]

Braid

[11] 4,090,970
[45] May 23, 1978

[54] ANTIOXIDANT COMPOSITIONS

[75] Inventor: Milton Braid, Westmont, N.J.

[73] Assignee: Mobil Oil Corporation, New York, N.Y.

[21] Appl. No.: 788,213

[22] Filed: Apr. 18, 1977

[51] Int. Cl.$^2$ .............. C10M 1/54; C10M 3/48; C10M 5/28; C10M 7/52

[52] U.S. Cl. .............. 252/42.7; 44/65; 44/68; 252/50; 252/52 R; 252/75; 252/400 R

[58] Field of Search .............. 252/42.7, 50, 52 R, 252/400 R, 75; 44/65, 68

[56] References Cited

U.S. PATENT DOCUMENTS

| | | | |
|---|---|---|---|
| 2,738,331 | 3/1956 | Brooks | 252/48.2 |
| 2,971,941 | 2/1961 | Fuchman et al. | 260/439 R |
| 3,398,170 | 8/1968 | Cyba | 252/400 R |
| 3,445,391 | 5/1969 | Braid et al. | 252/51.5 R |
| 3,557,225 | 1/1971 | Kubicek | 252/400 R |
| 3,636,022 | 1/1972 | Bright | 252/400 R |
| 3,692,738 | 9/1972 | Mathis et al. | 252/400 R |
| 3,816,492 | 6/1974 | Stretanski et al. | 252/400 R |

*Primary Examiner*—Delbert E. Gantz
*Assistant Examiner*—Irving Vaughn
*Attorney, Agent, or Firm*—Charles A. Huggett; Raymond W. Barclay; Howard M. Flournoy

[57] ABSTRACT

Compositions having excellent antioxidant characteristics are provided comprising organic media, normally susceptible to oxidation, e.g., oils of lubricant viscosity or greases prepared therefrom, containing a minor amount sufficient to impart antioxidant properties thereto of a mixture of certain organosulfur containing nickel complexes in combination with aryl amines, hindered phenols, quinones or mixtures thereof.

44 Claims, No Drawings

ANTIOXIDANT COMPOSITIONS

BACKGROUND OF THE INVENTION

1. Field of the Invention

This application is directed to compositions having excellent antioxidant characteristics comprising organic media normally susceptible to oxidation such as oils and greases of lubricating viscosity and various other functional fluids including mineral and synthetic hydrocarbon fluids, also plastics and rubbers which contain an amount sufficient to impart antioxidant properties thereto of a mixture of certain nickel organosulfur containing complexes in combination with arylamines and/or hindered phenols and quinones.

2. Description of Prior Art

It is known to use mixtures of sulfur containing compounds, e.g. diesters of thiodicarboxylic acids and hindered phenols to stabilize organic polymers against exposure to light and air; U.S. Pat. Nos. 3,644,282 and 3,652,495. It is also known to use arylamines such as phenyl naphthylamines as antioxidants for lubricating oils and for various polymers; U.S. Pat. Nos. 3,649,690, 3,781,361. It is also known to use nickel compounds, e.g., bis(stilbenedithiolato) nickel as an antioxidant for plastic materials; British Pat. No. 1,263,910 (1972).

SUMMARY OF THE INVENTION

This application, however, is directed to the discovery that compositions of improved antioxidant characteristics are provided when a mixture of certain organo nickel complexes, and/or arylamines, hindered phenols, quinones or mixtures thereof are combined in appropriate amounts.

The application is therefore directed to compositions comprising a major proportion of an organic medium normally susceptible to oxidation and a minor proportion sufficient to impart antioxidant properties thereto of a mixture soluble therein consisting essentially of an organosulfur containing nickel complex as described herein in combination with an arylamine and/or a hindered phenol and/or a quinone.

Accordingly, this application is more particularly directed to a lubricant composition comprising a major amount of a lubricant base and a minor amount effective for stabilizing said composition against oxidative degradation of a nickel complex selected from the group consisting of nickel thiobis-alkylphenolates, nickel thiobis-alkylphenol-phenolates and amine complexes of nickel thiobis-alkylphenolates wherein the alkyl groups thereof have from 1 to about 30 carbon atoms in combination with the above-referred to coadditives.

DESCRIPTION OF SPECIFIC EMBODIMENTS

The nickel complexes in accordance with the herein disclosed invention are particularly effective against oxidative degradation in such organic media as, for example, oils of lubricating viscosity, and other lubricating media and/or functional fluids such as hydrocracked lubricating oils, hydraulic oils, mineral or synthetic oils or fractions thereof, automotive oils, gear oils, transmission fluids, waxes, greases and other forms of lubricant compositions normally requiring the presence of an antioxidant to prevent and/or inhibit the degradative effect of oxidation.

The organosulfur-containing nickel complexes and the co-additives, i.e., arylamines, hindered phenols, quinones or mixtures thereof can be effectively employed in any amount which is sufficient for imparting to the herein-embodied compositions the desired degree of antioxidant protection. In many instances, the nickel complex is effectively employed in an amount from about 0.01 to about 5% by weight, and preferably in an amount from about 0.1 to about 2% by weight of the total weight of for example a lubricant composition. The term "nickel complex", as used herein is also intended to include nickel compounds having a chelate ring formation. The arylamines, hindered phenols and quinones each can be effectively employed in the same weight ratios as the nickel complex that is from about 0.01 to about 5% by weight of each, and preferably from about 0.1 to about 2% of each, by weight, of the total weight of the described compositions. Accordingly, the compositions in accordance herewith can contain from about 0.04 to about 20% by weight of the additive combination of organo nickel complex, arylamine, hindered phenol or quinone and from about 0.04 to 10 weight % of the nickel complex and an arylamine, hindered phenol or quinone. Preferably, however, the compositions contain from about 0.5 to 2.5 to 1 wt. % of nickel complex to arylamine, hindered phenol, or quinone on a molar basis and preferably from 0.5 - 1.5 to 1.

As hereinafter indicated, the organic sulfur-containing nickel complexes may be incorporated in lubricating media which includes mineral and synthetic base oils of lubricating viscosity and/or greases in which any of the aforementioned oils are employed as vehicles. Therefore, synthetic oils can also be effectively protected against oxidative degradation or may also be employed in combination with mineral oils, or as grease vehicles. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxy phenyl) ether, phenoxy phenylether, etc.

Particularly desirable organic sulfur-containing nickel complexes in accordance with the present invention include nickel thiobisphenolates, nickel thiobisphenol-phenolates, (thiobis-alkylphenolato) alkylamine nickel, (thiobis-alkyl phenolato) arylamine nickel.

Nickel thiobis-alkylphenolates may be employed having for example, the structure:

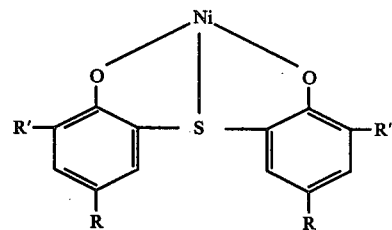

in which R' is hydrogen or a primary or secondary alkyl group having from 1 to about 30 carbon atoms, and R is an alkyl group having from 1 to about 30 carbon atoms in which the hydrogen atoms of the ring-attached carbon have been substituted by methyl ($CH_3$) or larger alkyl groups (e.g., $C_8H_{17}$).

Representative of the nickel thiobisphenolates is a nickel thiobisalkylphenolate, nickel 2,2'thiobis-(4-t-octyl) phenolate, having said structure in which R' is $C_8H_{17}$, 1,1,3,3-tetramethylbutyl or other 1,1-dimethylhexyl isomer.

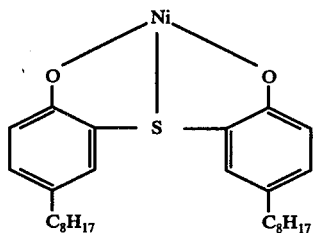

Nickel thiobis-alkylphenol-phenolates may be employed herein having, for example, the structure:

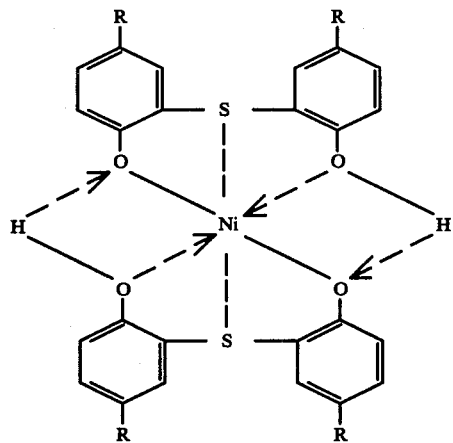

in which R is an alkyl group having from 1 to about 30 carbon atoms.

Representative of the nickel thiobis-alkyl phenol-phenolates is nickel 2,2'thiobis-(4-t-octyl) phenol-phenolate having the above structure II in which R is $C_8H_{17}$, 1,1,3,3-tetramethylbutyl or other 1,1-dimethylhexyl alkyl group.

Structure II can be converted in certain solvents such as ethanol, methanol, 2-propanol and acetone to structure I with the extrusion of thiobis-alkylphenol.

Representative of the nickel thiobis-alkyl phenolate and alkylamines is [2,2'-thiobis-(4-tert-octylphenolato)]-n-butylamine nickel having the structure:

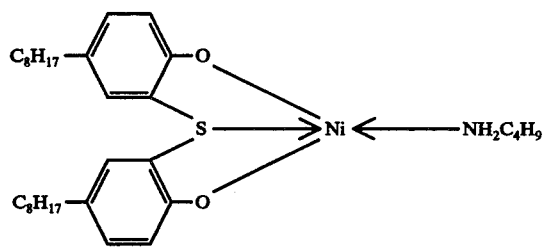

and its homolog [2,2'-thiobis-(4-tert-octylphenolato)]-n-octylamine nickel and its analog [2,2'-thiobis-(4-tert-octylphenolato)]- pyridine nickel.

Representative of other nickel thiobis alkylphenolate amine complexes is the aniline nickel thiobis alkylphenolate [2,2'-thiobis-(4-tert-octylphenolato)]-aniline nickel having the structure:

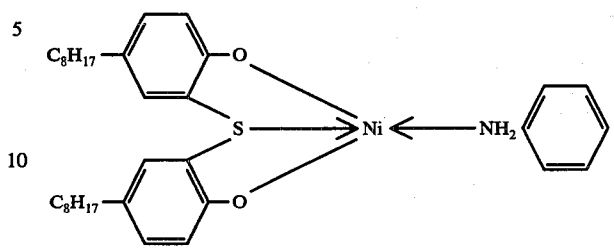

The arylamines used herein are preferably selected from the group consisting of the following: N-phenyl-1-naphthylamine; N-(4'-t-octylphenyl)-1-naphtylamine; N-phenyl-2-naphthylamine; 4,4'-thiobis(N-phenyl-1-naphthylamine); 1,1'-thiobis(N-phenyl-2-naphthylamine); diphenylamine; 4,4'-di-t-octyldiphenylamine; dinaphthylamine; 4-decoxydiphenylamine; phenothiazine. Especially preferred are phenyl naphthylamines such as N-phenyl-1-naphthylamine, N-(4-t-octylphenyl)-1-naphthylamine and N-phenyl-2-naphthylamine. However, it is understood that this is a non-limiting list and any arylamine appropriate in view of those disclosed above may be used. For purposes of this application it is understood that the term arylamines is meant to include arylaminoquinones, arylaminohydroquinones and phenothiazines.

Any suitable hindered phenolic compound may be used herein. Preferred are those selected from the following non-exhaustive list: 2,6-di-t-butyl-p-cresol; 4,4'-methylenebis (2-6-di-t-butyl-m-cresol); 4,4'-butyl idenebis(6-t-butyl-m-cresol) 4,4'-methylenebis-(2,6-di-t-butylphenol); 2,6-di-t-butylphenol, and 4,4'buty lidinebis-(2,6-di-t-butyl-phenol) 2,4,6-tri-t-butylphenol. Especially preferred is 4,4'-methylenebis-(2,6-di-t-butylphenol).

Suitable quinones or hydroquinones include 2-phenylthioquinone, 2,5-bisphenylthioquinone, alkylthiohydroquinones described in U.S. Pat. No. 2,738,331, 2,5-bis-t-octylaminobenzoquinone, 2,5-bis-dibutylaminoquinones and other aminoquinones, naphthoquinones or substituted derivatives thereof as described in U.S. Pat. No. 3,445,391.

In order to evaluate the effectiveness of compositions comprising the organosulfur-containing nickel complexes in combination with arylamines and/or hindered phenols or quinones as disclosed in the present invention the additives identified in the Tables below were tested in accordance with the following evaluation procedures (the amines, hindered phenols, quinones and the nickel complexes unless otherwise indicated were generally from commercial sources).

Catalytic Oxidation Test

A sample of the base lubricant is placed in an oven at a desired temperature. Present in the sample are the following metals either known to catalyze organic oxidation or commonly used materials of construction.
a. 15.6 sq. in. of sand-blasted iron wire,
b. 0.78 sq. in. of polished copper wire,
c. 0.87 sq. in. of polished aluminum wire and
d. 0.167 sq. in. of polished lead surface.
Dry air is passed through the sample at a rate of about 5 liters per hour.

One group of additives (Table 1) was tested in a solvent refined mineral oil. A second group (Tables 2 and 3) was tested in the presence of a synthetic lubricant comprising a pentaerythritol ester prepared from a mixture of $C_5$–$C_9$ or $C_5$ and $C_9$ monocarboxylic acids. The first group (Table 1) was tested at 325° F with a 40-hour air treatment and the second group (Tables 2 and 3) were tested at 450° F with a 24 hour air treatment. The samples are observed for increase in acidity (NN) and kinematic viscosity (KV) before and after treatment, the loss in weight of the lead specimen and the relative amount of visual sludge. The results are tabulated in said Tables 1, 2 and 3 respectively.

TABLE 1

Catalytic Oxidation Test
40 Hr., 325° F in Mineral Oil Base Stock[1]

| Ex. | Additive | Conc. nickel complex, wt. % | Conc. co-additive wt. % | Oxidized Oil ΔKV, Pb Loss | | | |
|---|---|---|---|---|---|---|---|
| | | | | ΔNN | % | mg | Sludge |
| 1 | None | — | — | 17 | 334 | 66 | Heavy |
| | | | | 17.8 | 202 | 171.3 | Light |
| 2 | [2,2'thiobis-(4-t-octylphenolato)]-n-butylamine nickel | 2 | — | 11.8 | 46 | 2.3 | Heavy |
| | | 1 | — | 4.64 | 19 | 1.3 | Heavy |
| | | 0.5 | — | 3.70 | 14 | 1 | Heavy |
| 3 | Ex. 2 + coadditive N-4'-t-octylphenyl)-1-naphthylamine | 1 | 1 | 0.61 | 9 | 0.1 | Nil |
| 4 | Ex. 2 + coadditive PAN (N-phenyl-1-naphthylamine) | 2 | 0.5 | 0.49 | 13 | 0.2 | Trace |
| | | 1 | 0.5 | 0.71 | 14 | 0.1 | Heavy |
| | | 0.5 | 0.5 | 4.44 | 19 | 0.3 | Heavy |
| 5 | Ex. 2 + coadditive 4,4'di-t-octyldiphenylamine | 2 | 1 | 3.86 | 21 | 0.2 | Trace |
| | | 1 | 1 | 3.57 | 21 | 0.2 | Heavy |
| | | 0.5 | 1 | 3.16 | 13 | 0.6 | Heavy |
| 6 | Ex. 2 + coadditive 4,4'di-t-octyldiphenylamine | 2 | 0.5 | 2.87 | 23 | 0.3 | Trace |
| | | 1 | 0.5 | 5.22 | 18 | 0.3 | Heavy |
| 7 | Ex. 2 + coadditive 2,6-di-t-butyl-4-methylphenol | 2 | 0.5 | 8.06 | 55 | 0.6 | Heavy |
| | | 1 | 0.5 | 6.03 | 28 | 0.7 | Heavy |
| | | 0.5 | 0.5 | 6.45 | 27 | 0.7 | Heavy |
| 8 | Ex. 2 + coadditive 4,4'-methylene-bis-2,6-di-t-butylphenol | 2 | 0.5 | 7.56 | 49 | 0.2 | Mod. |
| | | 1 | 0.5 | 8.19 | 32 | 0.4 | Heavy |
| | | 0.5 | 0.5 | 6.54 | 36 | 0.8 | Heavy |
| 9 | [2,2'-thiobis-(4-t-octylphenolato)]-n-octylamine nickel | 2 | — | 5.8 | 27 | 5.8 | Heavy |
| | | 1 | — | 5.5 | 21 | 44.4 | Heavy |
| | | 0.5 | — | 4.98 | 14 | 6.3 | Heavy |
| 10 | Ex. 9 + coadditive PAN | 2 | 0.5 | 1.6 | 25 | 0.3 | Moderate |
| | | 1 | 0.5 | 5.2 | 30 | 0.1 | Heavy |
| | | 0.5 | 0.5 | 8.4 | 37 | 1.7 | Heavy |

[1]The base stock was characterized by a viscosity of 4.95 Cs. at 210° F.

TABLE 2

Catalytic Oxidation Test
24 Hr. Ester Blends, 450° F

| Ex. | Additive | Conc. nickel complex, wt. % | Conc. co-additive wt. % | Oxidized Oil ΔKV, Pb Loss | | | |
|---|---|---|---|---|---|---|---|
| | | | | ΔNN | % | mg | Sludge |
| 1 | None | — | — | 8.25 | 586 | 13.7 | Trace |
| 2 | [2,2'-thiobis-(4-t-octylphenolato)]-n-butylamine nickel | 2 | — | 6.6 | 107 | 14.7 | Nil |
| | | 1 | — | 8.9 | 127 | 9.6 | Nil |
| | | 0.5 | — | 7.9 | 383 | 10 | Trace |
| 3 | N-phenyl-1-naphthylamine | — | 2 | 3.6 | 82 | 0.2 | Light |
| | | — | 1 | 4.1 | 97 | 0.4 | Light |
| 4 | 2:1 (w/w) Mixture of Ex. 2 + coadditive Ex. 3 | 2 | 1 | 2.96 | 60 | 1 | Trace |
| | | 1 | 0.5 | 3.99 | 54 | 2.8 | Nil |
| 5 | 1:1 (w/w) Mixture of Ex. 2 + coadditive Ex. 3 | 1.5 | 1.5 | 2.7 | 33 | 1.1 | Mod. |
| | | 0.75 | 0.75 | 4.4 | 78 | 2.2 | Nil |
| | | 0.375 | 0.375 | 2.7 | 48 | 2.5 | Trace |
| 6 | 1:1 (w/w) Mixture of Ex. 2 + coadditive Ex. 3 | 0.5 | 0.5 | 3.3 | 80 | 0.6 | Trace |
| | | 1 | 1 | 3.7 | 59 | 1.1 | Heavy |
| 7 | Ex. 4 + coadditive 4,4'-di-t-octyldiphenylamine | 1 | 1 | 2.6 | 51 | 0.9 | Nil |
| | | 0.5 | 1 | 3.8 | 77 | 1.0 | Trace |
| 8 | Ex. 5 + coadditive 4,4'di-t-octylidiphenylamine | 1 | 1 | 4.1 | 68 | 0.7 | Trace |
| | | 0.75 | 1 | 2.4 | 49 | 1.2 | Nil |
| | | 0.37 | 1 | 3.6 | 78 | 1 | Trace |
| 9 | Mixture of Ex. 5 + coadditive 4.4'-di-t-octyldiphenylamine | 1 | 1 | 2.4 | 46 | 2 | Trace |
| | | 0.5 | 0.5 | 4.9 | 56 | 1.7 | Trace |
| | | 0.25 | 0.25 | 4.1 | 114 | 1.2 | Trace |
| 10 | Ex. 2 + coadditive N-(4'-t-octylphenyl)-1-naphthylamine | 1 | 0.5 | 5.53 | 60 | 0.6 | Nil |
| 11 | Ex. 2 + coadditive N-(4'-t-octylphenyl)-1-naphthylamine | 0.5 | 1 | 5.06 | 120 | 0.6 | Nil |
| 12 | Ex. 2 + coadditive N-(4'-t-octylphenyl)-1-naphthylamine | 0.5 | 0.5 | 5.04 | 125 | 0.8 | Nil |
| 13 | Ex. 2 + coadditive 4-Decoxydiphenylamine | 1 | 2 | 4.52 | 73 | 0.9 | Trace |
| 14 | PTZ (Phenothiazine) | 2 | — | 2.97 | 63 | 0 | Heavy |
| | | 1 | — | 5.09 | 70 | 0.3 | Heavy |
| 15 | Ex. 2 + coadditive Ex. 14 | 2 | 1 | 2.65 | 57 | 1.4 | Trace |
| | | 1 | 1 | 2.18 | 58 | 2 | Mod. |
| 16 | Ex. 2 + coadditive Ex. 14 | 2 | 0.5 | 3.05 | 50 | 3.3 | Trace |
| | | 1 | 0.5 | 3.07 | 49 | 1.8 | Nil |
| 17 | Ex. 2 + coadditive 4,4'-methylenebis-2,6-di-t-butylphenol | 2 | 2 | 3.59 | 52 | 1.4 | Nil |
| | | 1 | 2 | 4.12 | 73 | 2.2 | Nil |

TABLE 2-continued

Catalytic Oxidation Test
24 Hr. Ester Blends, 450° F

| Ex. | Additive | Conc. nickel complex, wt. % | Conc. co-additive wt. % | ΔNN | Oxidized Oil ΔKV, % | Pb Loss mg | Sludge |
|---|---|---|---|---|---|---|---|
| 18 | Ex. 2 + coadditive 4,4'-methylenebis-2,6-di-t-butylphenol | 2 | 1 | 3.76 | 55 | 1.4 | Trace |
|  |  | 1 | 1 | 4.10 | 76 | 2.3 | Trace |

TABLE 3

Catalytic Oxidation Test
24 Hr. Ester Blends, 450° F

| Ex. | Additive | Conc. nickel complex, wt.% | Conc. co-additive wt.% | ΔNN | Oxidized Oil ΔKV, % | Pb Loss mg | Sludge |
|---|---|---|---|---|---|---|---|
| 1 | None | — | — | 8.25 | 586 | 13.7 | Trace |
| 2 | [2,2'-thiobis-(4-t-octylphenolato)]-n-butylamine nickel | 2 | — | 6.6 | 107 | 14.7 | Nil |
|  |  | 1 | — | 8.9 | 127 | 9.6 | Nil |
|  |  | 0.5 | — | 7.9 | 383 | 10 | Trace |
| 3 | Ex. 2 + coadditive 2,5-bis-t-octylaminobenzoquinone | 2 | 0.5 | 5.6 | 57 | 1.4 | Trace |
|  |  | 1 | 0.5 | 7.3 | 62 | 3.7 | Trace |
| 4 | Ex. 2 + coadditive of 2-phenyl-thiobenzoquinone | 2 | 0.5 | 7.5 | 57 | 2.4 | Trace |
|  |  | 1 | 0.5 | 7.6 | 68 | 0.7 | Trace |
| 5 | [2,2'-thiobis-(4-t-octylphenolato)]-n-octylamine nickel | 2 | — | 3.7 | 54 | 0.7 | Trace |
|  |  | 1 | — | 3.8 | 72 | 1 | Trace |
| 6 | N-phenyl-1-naphthylamine | — | 2 | 3.6 | 82 | 0.2 | Light |
|  |  | — | 1 | 4.1 | 97 | 0.4 | Light |
| 7 | Ex. 5 + coadditive Ex. 6 | 2 | 1 | 2.1 | 43 | 1.4 | Trace |
|  |  | 1 | 1 | 2.2 | 34 | 2.5 | Nil |
| 8 | Ex. 5 + coadditive Ex. 6 | 2 | 0.5 | 3.2 | 45 | 0.4 | Nil |
|  |  | 1 | 0.5 | 3.5 | 54 | 1.1 | Nil |
| 9 | [2,2'-thiobis-(4-t-octylphenolato]-pyridine nickel | 2 | — | 3.4 | 74 | 0.4 | Nil |
|  |  | 1 | — | 5.1 | 108 | 0.7 | Nil |
| 10 | [2,2'-thiobis-(4-t-octylphenolato)]-aniline nickel | 2 | — | 2.2 | 72 | 1.6 | Trace |
|  |  | 1 | — | 3.6 | 137 | 2.6 | Trace |
|  |  | 0.5 | — | 2.3 | 54 | 3.4 | Trace |
| 11 | Ex. 10 + coadditive Ex. 6 | 2 | 1 | 2.1 | 93 | 2.9 | Trace |
|  |  | 1 | 1 | 2.7 | 59 | 3.3 | Trace |
| 12 | Ex. 10 + coadditive Ex. 6 | 2 | 0.5 | 1.6 | 53 | 2.2 | Trace |
|  |  | 1 | 0.5 | 2.7 | 66 | 4 | Trace |
| 13 | 4,4'-di-t-octyldiphenylamine | 4 | — | 4.55 | 159 | 10.9 | Nil |
|  |  | 2 | — | 4.57 | 107 | 4.4 | Nil |
|  |  | 1 | — | 8.58 | 247 | 6.3 | Nil |
| 14 | Ex. 10 + coadditive Ex. 13 | 2 | 1 | 1.5 | 58 | 1.6 | Trace |
|  |  | 1 | 1 | 1.95 | 57 | 1.1 | Trace |
| 15 | Ex. 10 + coadditive N-(4'-t-octylphenyl9-1-naphthylamine | 2 | 1 | 0.96 | 55 | 1.3 | Trace |
|  |  | 1 | 1 | 1.8 | 55 | 2.3 | Trace |
| 16 | nickel 2,2'-thiobis-(4-t-octyl) phenol-phenolate | 2 | — | 4.19 | 92 | 1.3 | Nil |
|  |  | 1 | — | 4.98 | 119 | 1.4 | Nil |
|  |  | 0.5 | — | 3.87 | 100;11 | 1.3 | Trace |
| 17 | Ex. 16 + coadditive Ex. 6 | 2 | 1 | 1.55 | 45 | 2.6 | Nil |
|  |  | 1 | 1 | 2.9 | 49 | 39 | Nil |
| 18 | Ex. 16 + coadditive Ex. 6 | 2 | 0.5 | 2.55 | 54 | 2 | Nil |
|  |  | 1 | 0.5 | 4.39 | 74 | 3.7 | Nil |
| 19 | Ex. 16 + coadditive Ex. 13 | 2 | 1 | 1.61 | 66 | 1.9 | Nil |
|  |  | 1 | 1 | 3.73 | 87 | 1.4 | Nil |
|  |  | 0.5 | 1 | 2.68 | 69 | 0.5 | Nil |
| 20 | Ex. 16 + coadditive Ex. 13 | 2 | 1 | 2.98 | 68 | 1.2 | Nil |
|  |  | 1 | 1 | 4.4 | 90 | 1.9 | Nil |
|  |  | 0.5 | 1 | 3.71 | 88 | 1.3 | Nil |
| 21 | Ex. 16 + coadditive N-(4'-t-octylphenyl)-1-naphthylamine | 2 | 1 | 2.39 | 60 | 3.1 | Nil |
|  |  | 1 | 1 | 4.54 | 63 | 2.4 | Nil |
|  |  | 0.5 | 1 | 7.97 | 77 | 2.1 | Nil |
| 22 | Ex. 16 + coadditive N-(4'-t-octylphenyl)-1-naphthylamine | 2 | 0.5 | 3.41 | 67 | 3 | Nil |
|  |  | 1 | 0.5 | 2.62 | 34 | 2.1 | Nil |
|  |  | 0.5 | 0.5 | 3.75 | 92 | 1.8 | Nil |
| 23 | Ex. 16 + coadditive Ex. 6 + coadditive Ex. 13 | 2 | 2[1] | 1.79 | 48 | 1.8 | Trace |
|  |  | 1 | 2[1] | 3.58 | 70 | 2.2 | Nil |
|  |  | 0.5 | 2[1] | 3.47 | 81 | 3.1 | Nil |
| 24 | Phenothiazine | 2 | — | 2.97 | 63 | 0 | Heavy |
|  |  | 1 | — | 5.09 | 70 | 0.3 | Heavy |
| 25 | Ex. 16 + coadditive Ex. 24 | 2 | 1 | 2.57 | 65 | 1.1 | Nil |
|  |  | 1 | 1 | 3.14 | 59 | 1.3 | Nil |
|  |  | 0.5 | 1 | 3.46 | 44 | 0.5 | Heavy |
| 26 | Nickel 2,2'-thiobis-(4-t-octyl)-phenolate (Ex. 16 converted in 2-propanol | 2 | — | 4.3 | 87 | 0.5 | Trace |
|  |  | 1 | — | 5.5 | 137 | 1.2 | Nil |
| 27 | Ex. 26 + coadditive Ex. 6 | 2 | 1 | 2.8 | 76 | 0.1 | Light |
|  |  | 1 | 1 | 2.7 | 51 | 0 | Nil |
|  |  | 0.5 | 1 | 2.6 | 50 | 0 | Nil |
| 28 | Ex. 26 + coadditive Ex. 6 | 2 | 0.5 | 2.9 | 62 | 0.1 | Nil |
|  |  | 1 | 0.5 | 3.7 | 66 | 0 | Nil |
|  |  | 0.5 | 0.5 | 4.2 | 98 | 0 | Nil |
| 29 | Ex. 16 partially converted to Ex. 26 in acetone | 2 | — | 5.4 | 160 | 2.4 | Nil |
|  |  | 1 | — | 5.3 | 103 | 1.5 | Nil |

TABLE 3-continued

| | | Catalytic Oxidation Test 24 Hr. Ester Blends, 450° F | | | | | |
|---|---|---|---|---|---|---|---|
| | | Conc. nickel complex, | Conc. co-additive | | Oxidized Oil Δ KV, Pb Loss | | |
| Ex. | Additive | wt.% | wt.% | ΔNN | % | mg | Sludge |
| 30 | Ex. 29 + coadditive Ex. 6 | 1 | 0.5 | 3 | 62 | 3.6 | Nil |

(1)Test solution contains 1% by weight each of coadditives Ex. 6 and Ex. 13

The above results indicate that the additives of this invention are useful to prevent the oxidative breakdown of organic fluids and other organic media. After exposure to high temperature and air for extended periods of time, uninhibited mineral oils are especially susceptible to oxidation. The addition of a small amount of the novel compositions of this invention reduces their deterioration significantly. Additionally, the nickel complexes function as antisludging agents; see Table 3, Examples 6, 7 and 8 or 24 and 25, PAN or phenothiazine alone have visible sludge but PAN or phenothiazine plus an organo nickel complex in accordance herewith has little if any. These compositions may contain other additives which provide a variety of additional characteristics such as detergents, extreme pressure agents, pour point depressants, additional stability agents, viscosity control agents and the like.

This invention has been described with respect to the specific examples, however, the scope of the invention is not limited thereby.

What is claimed is:

1. A composition comprising a major proportion of an organic medium normally susceptible to oxidation and a minor proportion sufficient to impart antioxidant properties thereto of a mixture soluble therein consisting essentially of an organosulfur containing nickel complex selected from the group consisting of nickel thiobis-alkylphenolates, nickel thiobis-alkylphenol-phenolates and amine complexes of nickel thiobis-alkyl-phenolates, wherein the alkyl groups thereof have from 1 to about 30 carbon atoms, in combination with an arylamine, and/or a hindered phenol, and/or a quinone in which the weight ratio of organo nickel complex to arylamine, hindered phenol, or quinone is from about 0.01 – 5.0 to 1.

2. The composition of claim 1 wherein the arylamine is selected from the group consisting of aryl, diaryl, triaryl or alkaryl amines.

3. The composition of claim 2 wherein the arylamine is selected from N-phenyl-1-naphthylamine; N-phenyl-2-naphthylamine; N-(4-t-octylphenyl)-1-naphthyla-mine; 4,4'thiobis(N-phenyl-1-naphthylamine); 1,1'-thi-obis(N-phenyl-2-naphthylamine); 4,4'-di-t-octyldi-phenylamine; diphenylamine, 4-decoxydiphenylamine, triphenylamine, dinaphthylamine and phenothiazine.

4. The composition of claim 3 wherein the arylamine is N-phenyl-1-naphthylamine.

5. The composition of claim 3 wherein the arylamine is phenothiazine.

6. The composition of claim 3 wherein the arylamine is 4-decoxydiphenylamine.

7. The composition of claim 3 wherein the arylamine is 4,4'-di-t-octyldiphenylamine.

8. The composition of claim 1 wherein the hindered phenol is selected from the group consisting of 2,6-di-t-butyl-p-cresol; 4,4'-methylenebis- (2-6-di-t-butyl-m-cresol); 4,4'butyl idenebis-(6-di-t-butyl-m-cresol); 4,4'-methylenebis(2,6-di-t-butylphenol); 2,6-di-t-butyl-phenol and 4,4'-butyl lidenebis(2,6-di-t-butylphenol).

9. The composition of claim 8 wherein the hindered phenol is 4,4'-methylenebis-(2,6-di-t-butylphenol).

10. The composition of claim 1 wherein the nickel complex is (2,2'-thiobis-(4-tert-octylphenolato))-n-butylamine nickel.

11. The composition of claim 1 wherein the nickel complex is nickel 2,2'-thiobis(4-t-octyl) phenol-phenolate.

12. The composition of claim 1 wherein the nickel complex is nickel 2,2'-thiobis(4-t-octyl) phenolate.

13. The composition of claim 1 wherein the nickel complex is (2,2'-thiobis(4-tert-octylphenolato))aniline nickel.

14. The composition of claim 1 wherein the nickel complex is (2,2'-thiobis-(4-t-octylphenolato))-n-octyla-mine nickel.

15. The composition of claim 1 wherein the nickel complex is (2,2'-thiobis-(4-t-octylphenolato)) pyridine nickel.

16. The composition of claim 1 wherein the quinone is selected from the group consisting of 2,5-bis-t-octylaminobenzoquinone, 2,5-bis-t-butylaminoben-zoquinone, 2-phenylthiobenzoquinone, 2,5-bisphenyl-thiobenzoquinone, 2,5-bis-4-octylphenylthiobenzoqui-none, 2,5-bis-t-octylthiohydroquinone.

17. The composition of claim 13 wherein the quinone is 2-phenylthiobenzoquinone.

18. The composition of claim 13 wherein the quinone is 2,5-bis-t-octylaminobenzoquinone.

19. The composition of claim 1 wherein the organic medium is selected from the group consisting of oils of lubricant viscosity or greases prepared therefrom, fuel oils, hydrocracked oils, hydraulic oils, mineral oils or fractions thereof, automotive oils, gear oils, transmission fluids, or waxes.

20. The composition of claim 18 wherein the organic medium is an oil of lubricant viscosity.

21. The composition of claim 20 wherein the oil of lubricant viscosity is a mineral oil.

22. The composition of claim 20 wherein the oil of lubricant viscosity is a synthetic oil.

23. The composition of claim 22 wherein the synthetic lubricant has an ester base.

24. The composition of claim 18 wherein the lubricant composition is a grease.

25. An antioxidant additive mixture consisting essentially of an organosulfur containing nickel complex selected from the group consisting of nickel thiobis-alkylphenolates, nickel thiobis-alkylphenol-phenolates, amine complexes of nickel thiobis-alkylphenolates wherein the alkyl groups thereof have from 1 to about 30 carbon atoms in combination with an arylamine and-/or a hindered phenol and/or quinone in which the weight ratio of organo nickel complex to arylamine and/or hindered phenol or quinone is from about 0.01 – 5.0 to 1.

26. The mixture of claim 25 wherein the arylamine is selected from N-phenyl-1-naphthylamine; N-phenyl-2-naphthylamine; N-(4'-t-octylphenyl)-1-naphthylamine; 4,4'-thiobis-(N-phenyl-1-naphthylamine); 1,1'-thiobis-(N-phenyl-2-naphthylamine); 4,4'-di-t-octyldiphenylamine; diphenylamine; 4-decoxydiphenylamine; triphenylamine; dinaphthylamine and phenothiazine.

27. The mixture of claim 26 wherein the arylamine is N-phenyl-1-naphthylamine.

28. The mixture of claim 26 wherein said arylamine is phenothiazine.

29. The mixture of claim 26 wherein said arylamine is 4,4'-di-t-octyldiphenylamine.

30. The mixture of claim 25 wherein the hindered phenol is selected from the group consisting of 2,6-di-t-butyl-p-cresol; 4,4'-methylenebis-(2-6-di-t-butyl-m-cresol); 4,4'buty lidinebis(6-t-butyl-m-cresol); 4,4'-methylenebis(2,6-di-t-butylphenol); 2,6-di-t-butylphenol and 4,4'-buty lidinebis(2,6-di-t-butylphenol).

31. The mixture of claim 30 wherein the hindered phenol is 4,4'-methylenebis(2,6-di-t-butylphenol).

32. The mixture of claim 26 wherein the nickel complex is (2,2'-thiobis-(4-tert-octylphenolato))-n-butylamine nickel.

33. The mixture of claim 26 wherein the nickel complex is nickel 2,2'-thiobis(4-t-octyl) phenol-phenolate.

34. The mixture of claim 26 wherein the nickel complex is nickel 2,2'-thiobis(4-t-octyl) phenolate.

35. The mixture of claim 26 wherein the nickel complex is (2,2'-thiobis-(4-t-octylphenolato))-n-octylamine nickel.

36. The mixture of claim 26 wherein the nickel complex is (2,2'-thiobis-(4-t-octylphenolato)) aniline nickel.

37. The mixture of claim 25 wherein the amine complex of nickel thiobis-alkylphenolate is (2,2'-thiobis-4-t-octylphenolato))-n-butylamine nickel and the arylamine is selected from the group consisting of N-phenyl-1-naphthylamine; N-phenyl-2-naphthylamine; N-(4-t-octylphenyl)-1-naphthylamine; 4,4'thiobis (N-phenyl-1-naphthylamine); 1,1'-thiobis(N-phenyl-2-naphthylamine); 4,4'-di-t-octyldiphenylamine; diphenylamine, 4-decoxydiphenylamine, triphenylamine, dinaphthylamine and phenothiazine.

38. The mixture of claim 37 wherein the arylamine is N-(4'-t-octylphenyl)-1-naphthylamine.

39. The mixture of claim 37 wherein the arylamine is 4,4'-di-t-octyldiphenylamine.

40. The mixture of claim 37 wherein the arylamine is N-phenyl-1-naphthylamine.

41. The mixture of claim 37 wherein the arylamine is 4-decoxydiphenylamine.

42. The mixture of claim 37 wherein the arylamine is phenothiazine.

43. The mixture of claim 30 wherein the additive combination is (2,2'-thiobis-(4-t-octylphenolato))-n-butylamine nickel and 4,4'-methylenebis-2,6-di-t-butylphenol.

44. The mixture of claim 25 wherein the nickel complex is selected from the group consisting of nickel 2,2'-thiobis-(4-t-octyl)phenol-phenolate; (2,2'-thiobis-(4-t-octylphenolato))aniline nickel; nickel 2,2'-thiobis-(4-t-octyl) phenolate; and wherein the arylamine is selected from the group consisting of N-phenyl-1-naphthylamine; 4,4'-di-t-octyldiphenylamine; N-(4'-t-octylphenyl)-1-naphthylamine; and phenothiazine.

* * * * *

UNITED STATES PATENT AND TRADEMARK OFFICE
CERTIFICATE OF CORRECTION

PATENT NO. : 4,090,970
DATED : May 23, 1978
INVENTOR(S) : MILTON BRAID

It is certified that error appears in the above-identified patent and that said Letters Patent are hereby corrected as shown below:

Column 7, Table 3, Example 15, under Additive, "(4'-t-octylpheny19" should read --(4'-t-octylphenyl)--.

Column, 7 Table 3, Example 16, under %, delete ";11" after 100.

Signed and Sealed this

Fifth Day of December 1978

[SEAL]

Attest:

RUTH C. MASON
Attesting Officer

DONALD W. BANNER
Commissioner of Patents and Trademarks